United States Patent
Zok et al.

(10) Patent No.: US 6,184,399 B1
(45) Date of Patent: Feb. 6, 2001

(54) PROCESS FOR PREPARING A FATTY ACYL ISETHIONATE SALT

(75) Inventors: Claus-Peter Zok, Niederzier; Franz Jansen, Inden-Pier; Albert van de Berg, Kreuzau, all of (DE)

(73) Assignee: Akzo Nobel NV, Arnhem (NL)

( * ) Notice: Under 35 U.S.C. 154(b), the term of this patent shall be extended for 0 days.

(21) Appl. No.: 09/397,981

(22) Filed: Sep. 16, 1999

Related U.S. Application Data

(63) Continuation of application No. PCT/EP98/00815, filed on Feb. 12, 1998.

(30) Foreign Application Priority Data

Mar. 20, 1997 (EP) .................................................. 97200817

(51) Int. Cl.$^7$ .................................................. C07B 45/00
(52) U.S. Cl. ............................................... 554/92; 554/96
(58) Field of Search ......................................... 554/92, 96

(56) References Cited

U.S. PATENT DOCUMENTS

| | | | |
|---|---|---|---|
| 2,857,370 | 10/1958 | Sundberg | 260/97.5 |
| 3,320,292 | 5/1967 | Cahn et al. | 260/400 |
| 3,383,396 | 5/1968 | Cahn et al. | 260/400 |
| 3,394,155 | 7/1968 | Cahn et al. | 260/400 |
| 4,226,807 | 10/1980 | McCoy | 260/512 R |
| 4,571,309 | 2/1986 | Lege | 260/400 |

FOREIGN PATENT DOCUMENTS

| | | | |
|---|---|---|---|
| 0 246 471 | 11/1987 | (EP) | C07C/143/10 |
| 585071 | * 3/1994 | (EP) . | |
| 853590 | 11/1960 | (GB) . | |

OTHER PUBLICATIONS

*International Search Report*, Jun. 25, 1998.
*Ullmanns Encyklopädie der Technischen Chemie*, Band 20, Verlag Chemie, (1981), pp. 411–414.
Epton, S.R., "Methods of Analysis for Certain Surface Active Agents", *Nature*, vol. 160, pp. 795–796 (1947).
Rasmussen, H.T., "Analysis of Sodium Isethionate in Soap and Lye Process Streams by Suppressed Ion Chromatography", *Journal of American Oil Chemist Society*, vol. 70, pp. 733–764 (1993).

* cited by examiner

*Primary Examiner*—Deborah D. Carr
(74) *Attorney, Agent, or Firm*—Ralph J. Mancini; Lainie E. Parker

(57) ABSTRACT

A process is provided for preparing a fatty acyl isethionate salt of the formula $R^1C(O)OR^2SO_3M$ which comprises reacting at least one fatty acid of the formula $R^1C(O)OH$ with at least one hydroxyalkanesulfonic acid salt of the formula $HOR^2SO_3M$ in the presence of a catalyst, and distilling off water, wherein $R^1$ is a linear or branched, saturated or unsaturated hydrocarbon having 5 to 31 carbon atoms, $R^2$ is a linear, saturated or unsaturated hydrocarbon having 2 to 4 carbon atoms, and M is lithium, sodium, potassium, or ammonium and is characterised in that a foam control agent comprising a silicone oil is added. The foam control agent is added preferably once the reaction mixture is homogeneous. The process is suitably carried out with substantially equimolar amounts of fatty acid and hydroxyalkanesulfonic acid salt, preferably without distilling off any fatty acid.

8 Claims, No Drawings

PROCESS FOR PREPARING A FATTY ACYL ISETHIONATE SALT

This is a continuation of International application number PCT/EP98/00815 which was filed on Feb. 12, 1998.

FIELD OF THE INVENTION

The invention relates to a process for preparing a fatty acyl isethionate salt of the formula $R^1C(O)OR^2SO_3M$ wherein $R^1$ is a linear or branched, saturated or unsaturated hydrocarbon having 5 to 31 carbon atoms, $R^2$ is a linear, saturated or unsaturated hydrocarbon having 2 to 4 carbon atoms, and M is lithium, sodium, potassium, or ammonium.

BACKGROUND OF THE INVENTION

Such a direct esterification process is known from EP-A-0585071. This process is carried out at a temperature between about 180 and about 240° C. Some time after its start, the esterification reaction substantially ceases. Paraffin wax, which lowers the viscosity of the reaction mixture, is then added to the reaction mixture and esterification resumes. At the end of the reaction the pressure in the reaction vessel is lowered and the excess fatty acid is distilled off. During this distillation a foam is formed.

A disadvantage of the process of EP-A-0585071 is that in the course of the esterification reaction the reaction mass becomes exceedingly viscous, stirring the reaction mixture becomes difficult, and the reaction substantially ceases. The viscosity of the reaction mixture as such is not the problem. It is known in the art to add a viscosity reducing agent, as happens in the above-mentioned EP-A-0585071. In EP-A-0246471 a fluid, semi-solid or solid paraffin is added as a viscosity regulator. Alternatively, an excess of fatty acid is frequently used to keep the reaction mixture stirrable, as in GB 853590, U.S. Pat. No. 2,857,370, U.S. Pat. No. 3,320,292, U.S. Pat. No. 3,394,155, and U.S. Pat. No. 3,383,396.

We have found that the real problem resides in the combination of said viscosity and the formation of a foam, i.e., bubbles of reaction water vapour, which makes mixing of the contents of the reaction vessel difficult, if not impossible. Foaming starts as soon as the reaction product is being formed. As a consequence, the heat transfer is diminished, i.e., the reaction mixture darkens, and water is not distilled off any more, i.e., the reaction substantially ceases. The result is poor conversion and a product with a low active content.

In the process of EP-A-0585071 also during distillation of the excess fatty acid foaming occurs. It has to be monitored carefully by the operator in order for control over the reaction process to be maintained.

In the process of EP-A-0585071 a substantial amount (in examples 1 and 7 about 20 weight percent, based on sodium hydroxyethanesulfonate) of paraffin wax is added. Consequently, paraffin wax is always present in products obtained by this process. For some applications, there is a need for fatty acyl isethionate salts in which no paraffin wax, or for that matter any other consistency (or viscosity) regulator, is present. This for instance is the case with personal care products like shampoos, which need to be clear. It is an object of the present invention to provide a process in which the above-mentioned problems relating to foaming have been solved and which is suitably carried out without the addition of paraffin wax.

Although EP-A-0585071 mentions a molar ratio of the reactants of from about 2.0:1.0 to about 1.0:1.0, in each of the examples an excess of fatty acid is used and this excess is removed by distillation. In this context, we found that foaming became an even greater problem when substantially equimolar amounts of a fatty acid and a hydroxyalkanesulfonic acid salt are used.

In this respect, GB 853590 teaches that it is preferred to use an excess of the fatty acid. Excess fatty acid assists in maintaining the product in a liquid form during the reaction and also helps to prevent or greatly reduce the formation of foam. The same teaching, i.e., a 100% excess or more of fatty acid, is described in U.S. Pat. No. 2,857,370, U.S. Pat. No. 3,320,292, U.S. Pat. No. 3,394,155, and U.S. Pat. No. 3,383,396.

The use of substantially equimolar amounts of reactants is desired for an economical use of starting materials. Further, it is not necessary to distill off excess fatty acid, which results in short reaction times and in a product which has a high active content and is less odourous than the products obtained by the known processes. It is another object of this invention to provide a process in which substantially equimolar amounts of reactants can be used.

SUMMARY OF THE INVENTION

The invention generally relates to a process for preparing a fatty acyl isethionate salt of the formula $R^1C(O)OR^2SO_3M$ wherein $R^1$ is a linear or branched, saturated or unsaturated hydrocarbon having 5 to 31 carbon atoms, $R^2$ is a linear, saturated or unsaturated hydrocarbon having 2 to 4 carbon atoms, and M is lithium, sodium, potassium, or ammonium.

DETAILED DESCRIPTION OF THE INVENTION

As previously mentioned, invention relates to a process for preparing a fatty acyl isethionate salt of the formula $R^1C(O)OR^2SO_3M$ wherein $R^1$ is a linear or branched, saturated or unsaturated hydrocarbon having 5 to 31 carbon atoms, $R^2$ is a linear, saturated or unsaturated hydrocarbon having 2 to 4 carbon atoms, and M is lithium, sodium, potassium, or ammonium. The process comprises reacting at least one fatty acid of the formula $R^1C(O)OH$ with at least one hydroxyalkanesulfonic acid salt of the formula $HOR^2SO_3M$ in the presence of a catalyst, and distilling off water. The process is characterized by the use of a foam control agent comprising a silicone oil.

The addition of a foam control agent in the esterification reaction makes for a process where the reaction mixture stays stirrable throughout the reaction, yielding a product with a high active content.

Examples of fatty acids suitable for use in the process of the invention include compounds of the formula $R^1C(O)OH$, wherein $R^1$ has the definition described above. Particularly suitable are fatty acids wherein $R^1$ is a linear or branched, saturated or unsaturated hydrocarbon having 5 to 21 carbon atoms, more suitably having 7 to 17 carbon atoms. Preferred fatty acids are coconut fatty acid ($R^1$ having 7 to 17 carbon atoms), e.g., Kortacid C 70, hydrogenated coconut fatty acid ($R^1$ having 7 to 17 carbon atoms), palmitic acid ($R^1$ having 15 carbon atoms), palm kernel ($R^1$ having 7 to 17 carbon atoms), oleic acid (unsaturated $R^1$ having 17 carbon atoms), tallow fatty acid (partially unsaturated $R^1$ mainly having 16 and 18 carbon atoms), and hydrogenated tallow fatty acid. A particularly preferred fatty acid is coconut fatty acid. It will be known to one skilled in the art that naturally occurring fatty acids frequently are mixtures of acids having a hydrocarbon chain of varying length. It is within the scope of this invention to use naturally occurring fatty acids as well as synthetic fatty acids, or mixtures thereof.

Examples of hydroxyalkanesulfonic acid salts suitable for use in the invention process include compounds of the formula $HOR^2SO_3M$, wherein $R^2$ and M have the definitions described above. Sodium salts are preferred. Particularly suitable are hydroxyethanesulfonic acid salts. A particularly preferred hydroxyalkanesulfonic acid salt is sodium hydroxyethanesulfonate.

The reaction is performed without or preferably in the presence of a catalyst. Suitable catalysts include metallic oxides, such as zinc oxide, aluminium oxide, and magnesium oxide; inorganic acids, for example phosphoric acid, and sulfuric acid; organic acids like arylsulfonic acids, alkanesulfonic acids, and hydroxyalkanesulfonic acids, for example p-toluene sulfonic acid and 2-hydroxyethanesulfonic acid; metal salts, such as zinc sulfate, zinc isethionate, and aluminium sulfate. Mixtures of catalysts may also be used. Zinc oxide and phosphoric acid are particularly preferred catalysts. The catalyst is normally present in an amount of 0.05 to 2.0 weight percent, calculated on the total amount of fatty acid and hydroxyalkanesulfonic acid. Preferably, the catalyst is present in an amount of 0.05 to 0.5 weight percent.

Preferably, the esterification reaction is performed at a temperature of between 200 and 250° C. and a pressure of between $0.05 \times 10^5$ and $1 \times 10^5$ Pa. The reaction is more preferably carried out at a temperature of between 230 and 240° C.

For the purposes of this invention a foam control agent is defined as an agent which either prevents the formation of foam or which is able to degrade the foam once it has formed. Foam control agents, therefore, include foam inhibitors and defoamers. Foam control agents are known in the art (*Ullmanns Encyklopädie der Technischen Chemie*, Band 20, Verlag Chemie, 1981, p. 411–414) and are applied in a number of technological processes. The foam control agent according to the present invention comprises a silicone oil. The silicone defoamers used in the invention process are high-boiling, chemically inert, and colourless oils. The amount of silicone oil that needs to be present in the foam control agent of the invention process for effectively suppressing and/or preventing foam can easily be determined by a person skilled in the art by visual inspection of the reaction mixture. Examples of suitable foam control agents that may be used in combination with silicone oils in the invention process include mineral oils; fat derivatives, such as fatty acid esters and fatty acid amides; waxes, for example montan wax; phosphoric acid esters, natural or synthetic long-chain fatty alcohols; and water-insoluble polymers, for example polyalkyleneglycol ethers (*Ullmanns*, loc. cit.).

Examples of particularly suitable foam control agents comprising a silicone oil include neat silicone oils, i.e., linear and cyclic polyorganosiloxanes, for example dimethylpolysiloxanes; solutions of silicone oils and fatty acid esters, for example a 5–10% solution of a silicone oil in a fatty acid ester, such as coconut fatty acid methyl ester; and mixtures/formulations of silicone oils with other defoamers, for example paraffin oil. The foam control agent comprising a silicone oil may also be dispersed in the fatty acid that is used in the process of the invention. An example of a suitable commercially available silicone oil is Dow Corning 200 Fluid. An example of a commercially available mixture of silicone oil with paraffin oil is Byk 035.

The foam control agent comprising a silicone oil is added in the process of the invention in an amount effective for keeping foaming to a minimum. This can generally be achieved if the foam control agent comprising a silicone oil is present in an amount of 0.005 to 2.0 weight percent, calculated on the total weight of fatty acid and hydroxyalkanesulfonic acid salt. Preferred is an amount of 0.05 to 0.7 weight percent. The foam control agent can be added in one go or in portions and at the start of the reaction or during the reaction.

The process of the invention is suitably performed by mixing a fatty acid and a hydroxyalkanesulfonic acid salt with a selected catalyst and a foam control agent in a reaction vessel equipped with a stirrer, a thermometer, a subsurface nitrogen purge line, a condenser, and vacuum distillation piping with heat exchangers and vacuum receivers. The foam control agent may also be added during the esterification reaction. The starting materials can be added to the reaction vessel in any desired sequence.

The esterification reaction is carried out under an inert gas atmosphere, preferably nitrogen. An inert gas inhibits oxidation reactions of the reaction mixture. Such oxidation promotes poor colour and odour properties. The inert gas also acts as a carrier gas and aids the removal of water during distillation. The stirred reaction mixture is heated so that the temperature of the reaction mixture is raised to between 200 and 250° C., preferably to between 230 and 240° C. Once the reaction mixture has reached the desired temperature, the reaction is kept at it for several hours. Some reaction water is already being distilled off. Reaction times may vary depending on the reactants, the reaction temperature, and the amount of catalyst added. Under the preferred experimental conditions described herein reaction times are of the order of 3–10 hours in total. Vacuum is then applied in a stepwise fashion until a vacuum of between $0.05$–$0.10 \times 10^5$ Pa is reached, in order to prevent any fatty acid from being distilled off. The reaction water is removed from the reaction mixture by distillation. Subsequently, the reaction mass is cooled to about 70–100° C., the product is collected from the reaction vessel and cooled further to room temperature, using any suitable cooling equipment. It is preferred to extrude the reaction product.

Once the reactants and the catalyst have been mixed in the reaction vessel and the reaction temperature has been reached, the original heterogeneous reaction mixture is transformed into a homogeneous reaction mixture after a period of time, normally within 0.2 to 2 hours. It has been found advantageous to add the foam control agent as soon as the reaction mixture is homogeneous. In general, the process then can be continued without foaming occurring. Foaming can be easily observed visually. If necessary, an additional small amount of the foam control agent may be added to the reaction mixture. In the latter case, one skilled in the art will be able to determine the best moment of adding the foam control agent. The foam control agent can be added neat, as a solution, or as a dispersion. It is preferred to disperse the foam control agent in a retained small portion of the total amount of the fatty acid to be used and to add this dispersion to the reaction mixture, preferably during the reaction, and more preferably once a homogeneous reaction mixture is obtained.

The reaction mixture of the invention process may contain other conventional additives known to a skilled person, for example, a consistency regulator, such as a paraffin wax, a paraffin oil, or a fatty acid ester.

As said above, in the processes of EP-A-0585071 and EP-A-0246471, it is necessary to add a paraffin as an additive to the reaction mixture. The process of the present invention is suitably carried out without the addition of a consistency regulator. This specific embodiment has the advantage that the product obtained by the invention process will be free of such additives.

The process according to the present invention is suitably performed with a molar ratio of between 1.3:1.0 and 0.75:1.0, related to fatty acid and hydroxyalkanesulfonic acid salt, respectively. It is preferably carried out with a molar ratio of between 1.2:1.0 and 0.85:1.0, and more preferably with substantially equimolar amounts, i.e., a molar ratio of between 1.05:1.0 and 0.90:1.0, related to fatty acid and hydroxyalkanesulfonic acid salt, respectively. The embodiment of the invention process using substantially equimolar amounts of reactants has the specific advantage that a high conversion of sodium isethionate is obtained, as high as 98% as determined by ion chromatography and a product with a surprisingly high active content, typically more than 90% as determined by Epton titration (see EXPERIMENTAL). Further, no fatty acid needs to be distilled off, providing for an economical use of starting materials, short reaction times, and high reactor yields. Also, the final product obtained by this embodiment process is substantially free of coloured by-products and is less odourous than the products obtained by the known processes.

The very small amount of foam control agent used during the reaction remains in the final product. The presence of a minor amount of a foam control agent in the product obtained by the process of the invention does not affect the quality, i.e., active content, colour, odour, or surfactant properties of the product. Further, the obtained product is very suitable for use in personal care products.

Nevertheless, for some applications it is desired to prepare products in which a certain amount of either fatty acid or hydroxyalkanesulfonic acid salt is still present in the final product. Such products may also be prepared following the process of the invention and using an excess of either fatty acid or hydroxyalkanesulfonic acid salt. In one such embodiment of the invention process, using an excess of fatty acid, distillation is carried out under such conditions, i.e., temperature and pressure, that no fatty acid, but only water, is distilled off. This embodiment has the specific advantage that reaction times are short and conversion rates and reactor yields are high, since no fatty acid needs to be distilled off.

The fatty acyl isethionate salts prepared by the process of this invention have surfactant properties and may be used for the production of personal care products, for example cosmetic formulations, such as solid bar soaps, i.e., synthetic detergents (syndets), and liquid cleaning formulations, such as shampoos, and may also be used as detergents.

The invention is illustrated by the following examples.

EXPERIMENTAL

Materials: Coconut fatty acid (Kortacid C 70, Akzo Nobel)
Sodium hydroxyethane-sulfonate (Hoechst AG)
Zinc oxide (Siegfried Jacob Metallwerke)
Silicone oil (Dow Corning 200 Fluid)

The active content of fatty acyl isethionate salt in the reaction product obtained by the invention process was determined by the two-phase methylene blue titration procedure for anionic surfactants, i.e., Epton titration, as described in Epton, S. R., "Methods of Analysis for Certain Surface Active Agents," Nature, Vol. 160, page 795 (1947).

Reaction conversion was determined by analysis of the amount of sodium hydroxyethanesulfonate by means of ion chromatography as described in Rasmussen, H. T., "Analysis of sodium isethionate," Journal of the American Oil Chemist Society, Vol. 70, pages 733–734 (1993).

EXAMPLE 1

A 1 liter three-necked flask equipped with a stirrer, a thermometer, and a condenser was charged with 203.3 g (0.98 mole) of coconut fatty acid, 148 g (1 mole) of sodium hydroxyethanesulfonate, and 0.35 g of zinc oxide. The reaction vessel was purged with dry nitrogen and heated to 235° C. in 45 min. A homogeneous reaction mixture was obtained and 3.6 g (0.05 weight percent calculated on the total weight) of silicone oil (as a 5% by weight dispersion in coconut fatty acid) were added. Reaction water from the esterification process began to distill off. After 1 h the pressure was reduced stepwise to $0.05 \times 10^5$ Pa. No foaming occurred during the distillation of reaction water. A distillate of 17.7 g was collected containing water with traces of fatty acid. After 6 h the vacuum was relieved with nitrogen gas and the reaction mass was cooled to about 70–100° C., the product was collected from the reaction vessel, and cooled further to room temperature. The isolated reaction product (336.9 g of a white solid) contained 90.0% of sodium cocoylisethionate as determined by Epton titration. A conversion of 98% of sodium isethionate was achieved, as determined by ion chromatography.

EXAMPLE 2

A 1 liter three-necked flask equipped with a stirrer, a thermometer, and a condenser was charged with 263.5 g (1.3 moles) of coconut fatty acid, 148 g (1 mole) of sodium hydroxyethanesulfonate, and 0.42 g of zinc oxide. The reaction vessel was purged with dry nitrogen and heated to 235° C. in 45 min. A homogeneous reaction mixture was obtained and 4.2 g (0.05 weight percent calculated on the total weight) of silicone oil (as a 5% by weight dispersion in coconut fatty acid) were added. Reaction water from the esterification process began to distill off. After 67 min the pressure was reduced stepwise to $0.085 \times 10^5$ Pa and the distillate (19 g) of reaction water with only traces of fatty acid was collected. No foaming occurred during the distillation of reaction water. After 6 h the vacuum was relieved with nitrogen gas and the reaction mixture was cooled to about 70–100° C., the product was collected from the reaction vessel, and cooled further to room temperature. The isolated reaction product (396.2 g of a white solid) contained 83.4% of sodium cocoylisethionate, as determined by Epton titration. A good conversion of sodium isethionate was achieved, since the product only contained 0.1% of sodium hydroxyethanesulfonate, as determined by ion chromatography.

EXAMPLE 3

A 1 liter three-necked flask equipped with a stirrer, a thermometer, and a condenser was charged with 185.3 g (0.9 mole) of coconut fatty acid, 148 g (1 mole) of sodium hydroxyethanesulfonate, and 0.33 g of zinc oxide. The reaction vessel was purged with dry nitrogen and heated to 235° C. in 45 min. A homogeneous reaction mixture was obtained and 2.33 g (0.7 weight percent calculated on the total weight) of silicone oil (neat) were added. Reaction water from the esterification process began to distill off. After 59 min the pressure was reduced stepwise to 50 mbar and the distillate (16.3 g) containing water with only traces of fatty acid was collected. No foaming occurred during the distillation of reaction water. After 6 h the vacuum was relieved with nitrogen gas and the reaction mass was cooled to about 70–100° C., the product was collected from the reaction vessel, and cooled further to room temperature. The reaction product isolated (318.4 g of a white solid) contained 90.0% of sodium cocoylisethionate, as determined by Epton titration. A good conversion of sodium isethionate was achieved, since the isolated product contained 2.7% free fatty acid, as determined by ion chromatography.

EXAMPLE 4

A 1 liter three-necked flask equipped with a stirrer, a thermometer, and a condenser was charged with 205.9 g (1 mole) of coconut fatty acid, 148 g (1 mole) of sodium hydroxyethanesulfonate, 0.35 g of zinc oxide, and 3.5 g (1.0 weight percent calculated on the total weight) of silicone oil. The reaction vessel was purged with dry nitrogen and heated to 235° C. in 45 min. A homogeneous reaction mixture was obtained. Reaction water from the esterification process began to distill off. After 1 h the pressure was reduced stepwise to $0.05 \times 10^5$ Pa. No foaming occurred during the distillation of reaction water. A distillate of 17.8 g was collected containing water with traces of fatty acid. After 6 h the vacuum was relieved with nitrogen gas and the reaction mass was cooled to about 70–100° C., the product was collected from the reaction vessel and cooled further to room temperature. The isolated reaction product contained 92.3% of sodium cocoylisethionate as determined by Epton titration.

COMPARATIVE EXAMPLE 1

A 1 liter three-necked flask equipped with a stirrer, a thermometer, and a condenser was charged with 226.5 g (1.1 moles) of coconut fatty acid, 148 g (1 mole) of sodium hydroxyethanesulfonate, and 0.37 g of zinc oxide. The reaction vessel was purged with dry nitrogen and heated to 235° C. in 45 min. A homogeneous reaction mixture was obtained. Reaction water from the esterification process began to distill off and strong foaming occurred. After 2 h of esterification black product particles were obtained. When the pressure was stepwise reduced to $0.8 \times 10^5$ Pa strong foaming occurred again, the volume of the reaction mixture was tripled and the condenser immediately was blocked so that the experiment had to be stopped. The obtained reaction product contained 68% of sodium cocoylisethionate as determined by Epton titration. A conversion of about 73% of sodium isethionate was achieved, as determined by ion chromatography.

COMPARATIVE EXAMPLE 2

A 1 liter three-necked flask equipped with a stirrer, a thermometer, and a condenser was charged with 226.5 g (1.1 moles) of coconut fatty acid, 148 g (1 mole) of sodium hydroxyethanesulfonate, and 0.37 g of zinc oxide. The reaction vessel was purged with dry nitrogen and heated to 235° C. in 45 min. A homogeneous reaction mixture was obtained. Reaction water from the esterification process began to distill off and strong foaming occurred. After 2.5 h of esterification black product particles were obtained. The foamy reaction mixture was stirred for an additional 3.5 h. The obtained reaction product contained 71.7% of sodium cocoylisethionate as determined by Epton titration.

COMPARATIVE EXAMPLE 3

Experiments performed by the Applicant have shown that foam control agents not containing a silicone oil, i.e., paraffin oil, polypropoxylate, fatty acid ester, phosphoric ester, and fluoro surfactant, did not sufficiently suppress foam formation during the preparation of fatty acyl isethionate salts.

We claim:

1. A process for preparing a fatty acyl isethionate salt of the formula $R^1C(O)OR^2SO_3M$ which comprises reacting a reaction mixture comprising at least one fatty acid of the formula $R^1C(O)OH$ with at least one hydroxyalkanesulfonic acid salt of the formula $HOR^2SO_3M$ in the presence of a catalyst, and distilling off water, wherein $R^1$ is a linear or branched, saturated or unsaturated hydrocarbon having 5 to 31 carbon atoms, $R^2$ is a linear, saturated or unsaturated hydrocarbon having 2 to 4 carbon atoms, and M is lithium, sodium, potassium, or ammonium, wherein a foam control agent comprising a silicone oil is added to the reaction mixture.

2. The process of claim 1 wherein the amount of foam control agent is 0.005 to 2.0 percent by weight, based on the total weight of fatty acid and hydroxyalkanesulfonic acid salt.

3. The process of claim 1 wherein the foam control agent is a solution of a silicone oil in a fatty acid ester.

4. The process of claim 1 wherein the foam control agent is added once the reaction mixture is homogeneous.

5. The process of claim 1 wherein no fatty acid is distilled off during or after the reaction.

6. The process of claim 1 wherein the molar ratio of fatty acid to hydroxyalkanesulfonic acid salt is in the range of from 1.3:1.0 to 0.75:1.0.

7. The process of claim 6 wherein the molar ratio is in the range of from 1.05:1.0 to 0.90:1.0.

8. The process of claim 6 wherein the molar ratio is in the range of from 1.05:1.0 to 0.90: 1.0.

* * * * *